US00PP37098P2

(12) United States Plant Patent
Ohashi et al.

(10) Patent No.: US PP37,098 P2
(45) Date of Patent: Nov. 18, 2025

(54) STRAWBERRY PLANT NAMED 'HOB-391'

(50) Latin Name: ***Fragaria* x *ananassa* Duchesne ex Rozier**
Varietal Denomination: HOB-391

(71) Applicant: HOB Co. Ltd., Kamikawa Hokkaido (JP)

(72) Inventors: Takafumi Ohashi, Chiba (JP); Yuhei Takeda, Hokkaido (JP); Marina Iwao, Hokkaido (JP)

(73) Assignee: HOB Co. Ltd., Higashikagura-cho (JP)

( * ) Notice: Subject to any disclaimer, the term of this patent is extended or adjusted under 35 U.S.C. 154(b) by 0 days.

(21) Appl. No.: 19/001,003

(22) Filed: Dec. 24, 2024

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Seckel IP, PLLC

(57) ABSTRACT

A new variety of strawberry plant named 'HOB-391' that has high hardness of fruit body, with the fruit having achenes positioned deep below the surface and a light red core.

3 Drawing Sheets

Common name: Strawberry

Botanical classification: *Fragaria* x *ananassa* Duchesne ex Rozier.

Variety denomination: 'HOB-391'.

CROSS-REFERENCE TO PRIOR APPLICATION

This application follows Japanese plant variety rights application No. 37439 filed May 24, 2024, the entire content of which is incorporated by reference herein.

BACKGROUND OF THE NEW VARIETY

The present invention relates to a new and distinct variety of strawberry, *Fragaria* x *ananassa* Duchesne ex Rozier, which has been given the variety denomination 'HOB-391'.

The variety is distinguished by its high hardness of fruit body and its good balance of sweetness and acidity, with the fruit having achenes positioned deep below the surface and a light red core, that distinguish it notably from its female parent 'Pechika Pure' (fruit having achenes positioned shallow below the surface and a white core).

ORIGIN OF THE VARIETY

The parent varieties are 'Akihime' (male parent) (not patented in the U.S.) and 'Pechika Pure' (female parent) (not patented in the U.S.).

The variety was developed and propagated in Higashikagura-cho, Kamikawa-gun, Hokkaido, Japan.

The new variety was asexually reproduced by runners in Higashikagura-cho, Kamikawa-gun, Hokkaido, Japan.

In March 2017, the mother variety 'Pechika Pure' and father variety 'Akihime' were crossed in a greenhouse in Higashikagura-cho, Kamikawa-gun, Hokkaido, Japan.

In 2017, the resulting seedlings were sown and raised.

In 2018, the raised seedlings were planted in a test field located in Higashikagura-cho, Kamikawa-gun, Hokkaido, Japan, and two individuals with superior characteristics were selected.

In 2019, the test was carried out again and 'HOB-391' was selected for its high hardness of fruit body and its taste.

On May 24, 2024, an application for plant variety rights No. 37439 was filed for the present variety in the Japanese Plant Variety Protection Office of the Ministry of Agriculture, Forestry and Fisheries (MAFF), Japan.

Cultivation of the variety does not require special conditions or treatments.

Proper planting time is from the end of March to the beginning of April.

Flowering time is from the middle of May.

Harvesting time is from the end of June to the end of November.

The variety is currently mainly intended for fruit production.

SUMMARY OF THE VARIETY

The variety is distinguished from its female parent 'Pechika Pure', which is its closest comparative cultivar, by its high hardness of fruit body and its good balance of sweetness and acidity, with the fruit having achenes positioned deep below the surface and a light red core, that distinguish it notably from its female parent 'Pechika Pure' (fruit having achenes positioned shallow below the surface and yellowish pink (RHS 33C) core). The variety is also distinguished from its male parent 'Akihime' by the position of achenes deep below the surface of the fruit and the moderate to large difference in shape of terminal and other fruits, that distinguish it notably from its male parent 'Akihime' (achenes below the surface of the fruit, slight difference in shape of terminal and other fruits).

A comparison table with the male parent 'Akihime' is as follows (evaluation based on averages).

TABLE 1

| | 'HOB-391' | 'Akihime' |
|---|---|---|
| Fruit: position of achenes | deep below surface | below surface |
| Difference in shape of terminal and other fruits | moderate to large | slight |
| Type of bearing | day neutral | not remontant |

A comparison table with the female parent 'Pechika Pure' is as follows (evaluation based on averages).

TABLE 2

| | 'HOB-391' | 'Pechika Pure' |
|---|---|---|
| Fruit: position of achenes | deep below surface | below surface |
| Color of core | light red (RHS 43C) | yellowish pink (RHS 33C) |

BRIEF DESCRIPTION OF THE DRAWINGS

In the accompanying drawings, which are as nearly true as is reasonable possible to make in a color illustration of this type.

Figure 1:
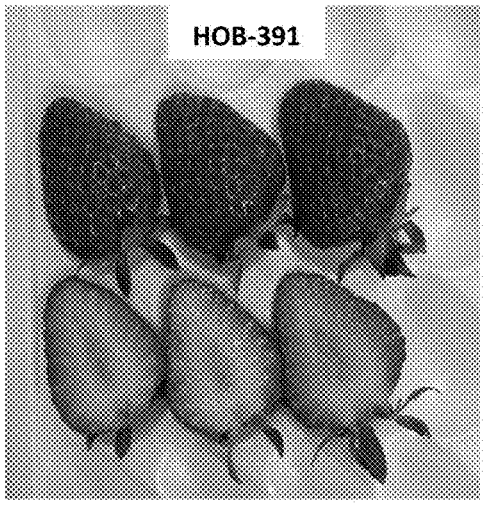
FIG. 1 is a color photograph showing fruit of 'HOB-391'.
Figure 2:
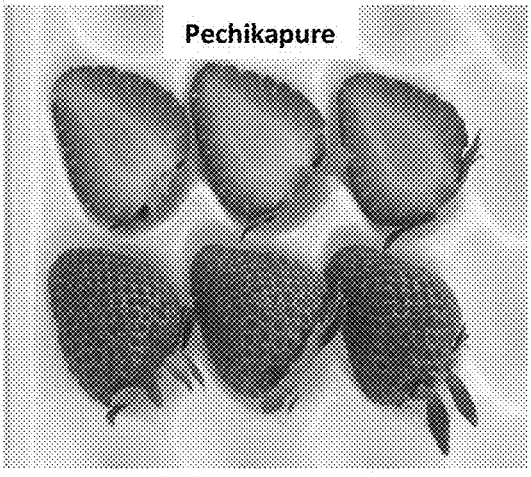
FIG. 2 is a color photograph showing fruit of 'Pechika Pure' for comparison purposes.
Figure 3:
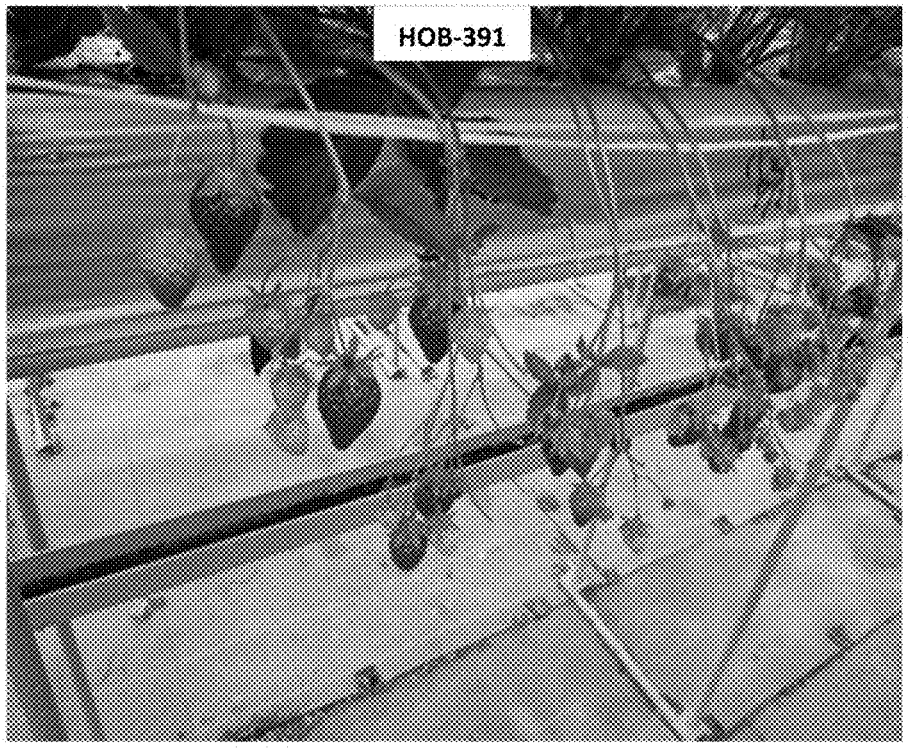
FIG. 3 is a color photograph showing the plant, leaves, and fruit of 'HOB-391'.
Figure 4:
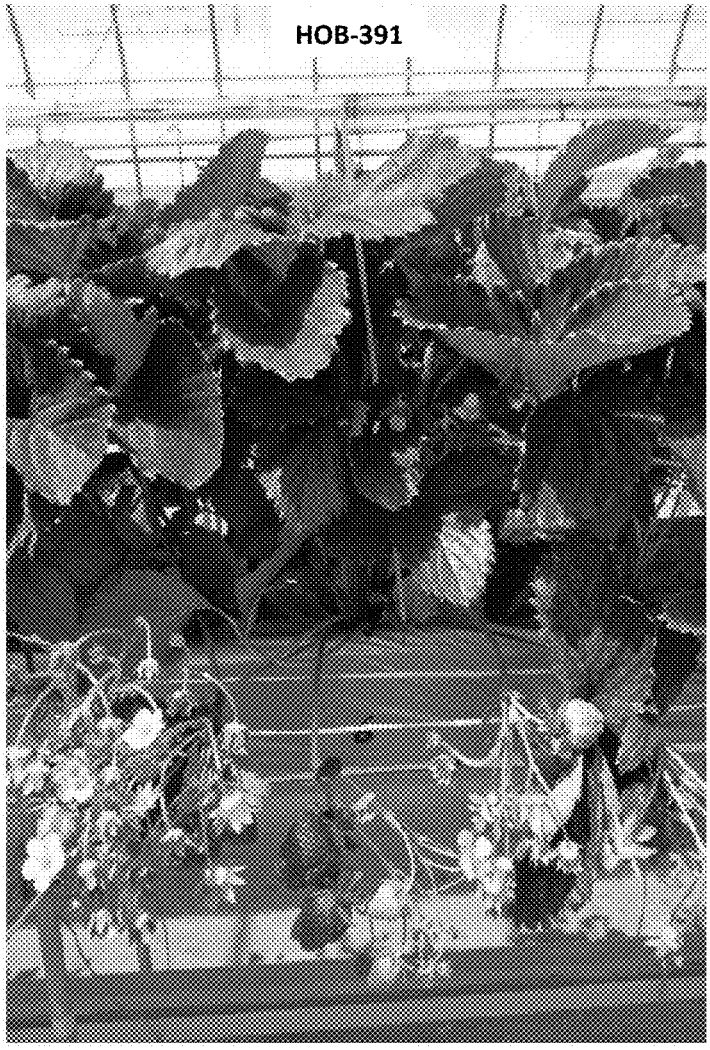
FIG. 4 is a color photograph showing the plant, leaves, flowers, and fruit of 'HOB-391'.
Figure 5:
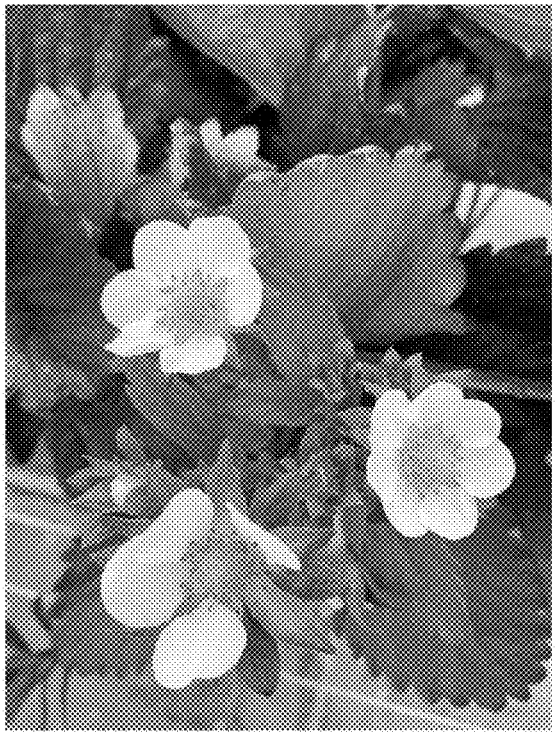
FIG. 5 is a color photograph showing the flowers of 'HOB-391'.
Figure 6:
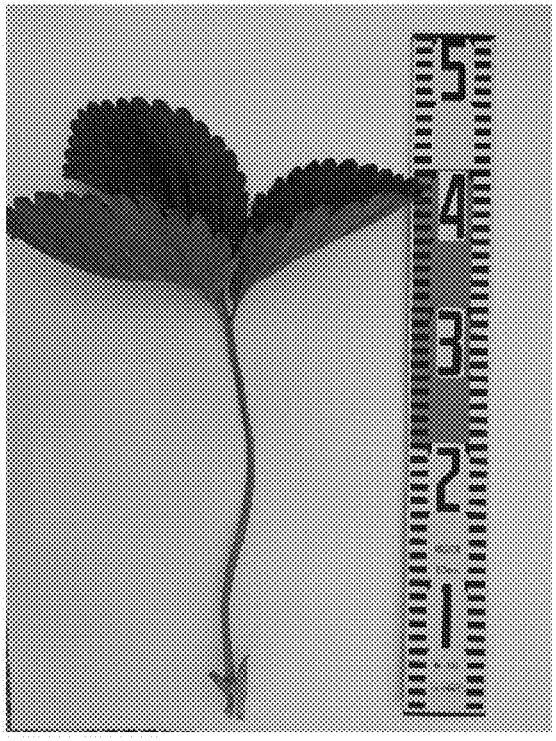
FIG. 6 is a color photograph showing the leaf of 'HOB-391'.

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'HOB-391' plants evaluated in 2023, including for the comparison with the female parent 'Pechika Pure'. Values as provided are averages.

The plants shown on the photographs were grown in Higashikagura-cho, Kamikawa-gun, Hokkaido, Japan. The plant is a 5-year grown plant.

Colors are given according to the RHS (Royal Horticultural Society) Colour Chart (Fourth Ed., 2001).

BOTANICAL DESCRIPTION

TABLE 3

| | Characteristics | States/Values |
|---|---|---|
| 1 | Plant | |
| 1.1 | Plant growth habit | upright |
| 1.2 | Density of foliage | medium to sparse |
| 1.3 | Vigor | medium to strong |

TABLE 3-continued

| | Characteristics | States/Values |
|---|---|---|
| 1.4 | Number of axillary bud | few |
| 1.5 | Position of inflorescence in relation to foliage | same level |
| 1.6 | Number of stolons | medium to many |
| 1.7 | Stolon: average length | 30 cm |
| 1.8 | Stolon: surface texture | rough |
| 1.9 | Stolon: color | strong yellowish green (RHS 134B) |
| 2 | Leaf | |
| 2.1 | Leaf size | medium (31cm$^2$) (length 24 cm, width 31 cm) |
| 2.2 | Color of upper side | dark green (RHS 146A) |
| 2.3 | Color of lower side | light yellowish green (RHS 135D) |
| 2.4 | Glossiness | medium |
| 2.5 | Blistering | absent or weak |
| 2.6 | Variegation | absent |
| 2.7 | Leaflet: number | 3 per leaf |
| 2.8 | Leaflet: length | 18 cm |
| 2.9 | Leaflet: width | 12 cm |
| 2.10 | Leaflet: apex | retuse |
| 2.11 | Leaflet: texture (upper side) | glossy |
| 2.12 | Leaflet: texture (lower side) | rough |
| 2.13 | Terminal leaflet: size | large (223.3 cm$^2$) |
| 2.14 | Shape of base | acute |
| 2.15 | Margin | serrate to crenate |
| 2.16 | Shape in cross section | concave |
| 3 | Stem | |
| 3.1 | Petiole: length | long (29.5 cm) |
| 3.2 | Petiole: diameter | 0.5 cm |
| 3.3 | Petiole: texture | hairy and rough |
| 3.4 | Petiole: color | strong yellowish green (RHS 134B) |
| 3.5 | Attitude of hairs | slightly outwards |
| 3.6 | Anthocyanin coloration | absent |
| 3.7 | Anthocyanin color | absent |
| 3.8 | Peduncle: length | medium (17.2 cm) |
| 3.9 | Peduncle: diameter | 0.3 cm |
| 3.10 | Peduncle: texture | hairy and rough |
| 3.11 | Peduncle: strength | strong (not removed from the crown at harvest) |
| 3.12 | Peduncle: color | strong yellowish green (RHS 134B) |
| 3.13 | Pedicel: attitude of hairs | slightly outwards |
| 3.14 | Pedicel: length | 2.5 cm |
| 3.15 | Pedicel: diameter | 0.2 cm |
| 3.16 | Pedicel: texture | hairy and rough |
| 3.17 | Pedicel: strength | strong and hard to break |
| 3.18 | Pedicel: color | greenish-blue (RHS 140C) |
| 4 | Flower | |
| 4.1 | Flower diameter | medium to large (4 cm) |
| 4.2 | Flower depth | 1.5 cm |
| 4.3 | Arrangement of petals | touching |
| 4.4 | Stamen | present |
| 4.5 | Petal: number | 8 per flower |
| 4.6 | Petal: shape | rounded equilateral triangle |
| 4.7 | Petal: length | 1.7 cm |
| 4.8 | Petal: width | 1.7 cm |
| 4.9 | Petal: apex | round |
| 4.10 | Petal: margin | retuse |
| 4.11 | Petal: base | flattened |
| 4.12 | Petal: texture of upper surface | smooth and moist |
| 4.13 | Petal: texture of lower surface | smooth and moist |
| 4.14 | Petal: color of upper side | white (RHS NN155D) |
| 4.15 | Petal: color of lower side | white (RHS NN155D) |
| 5 | Fruit | |
| 5.1 | Fruit weight | medium to small (29.8 g) (height 5.0 cm, width 4.0 cm) |
| 5.2 | Shape | conical |
| 5.3 | Shape at apex | acute or truncate |
| 5.4 | Shape at base | flattened |
| 5.5 | Color | red (RHS 50A) |
| 5.6 | Shape of achenes | narrow drops |
| 5.7 | Number of achenes | 150 per fruit |
| 5.8 | Number of berries | 15-20 per fruiting truss |

TABLE 3-continued

| | Characteristics | States/Values |
|---|---|---|
| 5.9 | Evenness of color | even or very slightly uneven |
| 5.10 | Evenness of surface | even or very slightly uneven |
| 5.11 | Neck | absent |
| 5.12 | Position of calyx attachment | level with fruit |
| 5.13 | Attitude of sepals | upwards |
| 5.14 | Sepal: number | 16 |
| 5.15 | Sepal: shape | narrow lenticular |
| 5.16 | Sepal: length | 1.5 cm |
| 5.17 | Sepal: width | 0.6 cm |
| 5.18 | Sepal: apex | acute |
| 5.19 | Sepal: margin | flattened |
| 5.20 | Sepal: base | retuse |
| 5.21 | Sepal: texture of upper surface | glossy |
| 5.22 | Sepal: texture of lower surface | glossy |
| 5.23 | Sepal: color of upper surface | strong green (RHS N134C) |
| 5.24 | Sepal: color of lower surface | light yellowish green (RHS 134D) |
| 5.25 | Firmness | medium |
| 5.26 | Color of flesh | light red (RHS N30B) |
| 5.27 | Color of core | light red (RHS 43C) |
| 5.28 | Cavity | absent or small |
| 6 | Fruit ripening | |

TABLE 3-continued

| | Characteristics | States/Values |
|---|---|---|
| 6.1 | Time of beginning of flowering | June 7 |
| 6.2 | Time of beginning of fruit ripening | June 27 |
| 6/3 | Time of beginning of harvest season | late June to late November |
| 6.4 | Type of bearing | day neutral |
| 6.5 | Soluble solids content | high (Brix = 10) |
| 6.6 | Acidity | medium to low (0.45%) |

Other features of the plant are as follows:

Plant hardiness zone of the plant: adapted to summer in cooler areas of Japan; has excellent heat resistance but poor cold resistance. In cold weather, the plants are dwarfed and the progress of fruit coloration is slow.

Disease and pest resistance: Normal resistance was observed for pests and diseases in Higashikagura-cho, Kamikawa-gun, Hokkaido, Japan.

We claim:

1. A new and distinct variety of strawberry plant named 'HOB-391', substantially as described and illustrated herein.

* * * * *